United States Patent [19]

Wheeler et al.

[11] Patent Number: 4,845,779
[45] Date of Patent: Jul. 11, 1989

[54] PROTECTIVE HOSPITAL GOWN

[76] Inventors: Ronald M. Wheeler, 31 Autumnwood Dr.; Joseph A. Germy, Jr., 220 Edgewood Terrace Dr., K24, both of Jackson, Miss. 39206

[21] Appl. No.: 177,821

[22] Filed: Mar. 24, 1988

Related U.S. Application Data

[63] Continuation-in-part of Ser. No. 107,901, Oct. 9, 1987, abandoned, which is a continuation-in-part of Ser. No. 91,755, Sep. 1, 1987, abandoned.

[51] Int. Cl.$^4$ .................. A41D 3/00; A41D 13/00
[52] U.S. Cl. ............................................. 2/84; 2/69; 2/DIG. 7
[58] Field of Search ................. 2/2, 2.1 R, 2.1 A, 69, 2/79, 84, 114, 171, 173, 202, 205, 206, DIG. 7

[56] References Cited

U.S. PATENT DOCUMENTS

| | | | |
|---|---|---|---|
| D. 208,527 | 9/1967 | Grengg | 2/48 |
| 1,466,726 | 9/1923 | Meeks | 2/84 |
| 1,560,997 | 11/1925 | Kelly | 2/48 |
| 1,691,472 | 11/1928 | Graham et al. | 2/69 |
| 2,331,283 | 10/1943 | Wheeler | 2/81 |
| 2,374,643 | 5/1945 | Boettcher | 2/DIG. 1 |
| 2,383,261 | 8/1945 | Kronhaus | 2/2.1 R |
| 2,492,003 | 12/1949 | Peckinpaugh | 2/51 |
| 3,045,815 | 7/1962 | Abildgaard | 2/2.1 R |
| 3,496,572 | 2/1970 | Herzig | 2/32 |
| 3,736,595 | 6/1973 | Siegmann | 2/2 |
| 3,855,635 | 12/1974 | Ramirez | 2/114 |
| 3,911,499 | 10/1975 | Benevento et al. | 2/114 |
| 3,943,575 | 3/1976 | Bolker | 2/DIG. 7 |
| 4,055,173 | 10/1977 | Knab | 2/DIG. 7 |
| 4,118,802 | 10/1978 | Polster | 2/84 |
| 4,408,357 | 10/1983 | Toth | 2/114 |
| 4,426,740 | 1/1984 | Reverberi | 2/84 |
| 4,513,452 | 4/1985 | Rankin, Sr. et al. | 2/84 |
| 4,586,196 | 5/1986 | White | 2/DIG. 7 |
| 4,677,696 | 7/1987 | Tanaka | 2/84 |

FOREIGN PATENT DOCUMENTS 1291012  3/1962  France .................... 2/84

OTHER PUBLICATIONS

Disposable Clothing-Industrial Safety & Security Co. (undated).

*Primary Examiner*—Werner H. Schroeder
*Assistant Examiner*—Jeanette E. Chapman
*Attorney, Agent, or Firm*—Laubscher, Presta & Laubscher

[57] ABSTRACT

A disposable hospital gown includes body, arm, and hood portions and gloves connected with the arm portions assembled so as to provide a unitary structure impervious to fluid. The hood portion contains an enlarged viewing opening in its front surface for receiving a clear plastic visor and a ventilating mask which are connected with the hood portion in sealing relation. A protective flap is sealed to the visor to cover the ventilating mask. The gown, hood and flap are formed of a barrier material which is impervious to bodily fluids and germs. A plurality of fasteners at the rear of the body portion close a vertical opening contained therein when the device is worn. The unitary gown thus protects the wearer's body from contact with any fluids expelled from a patient's body to prevent the transmission of any disease between the wearer and the patient.

34 Claims, 5 Drawing Sheets

FIG. 5
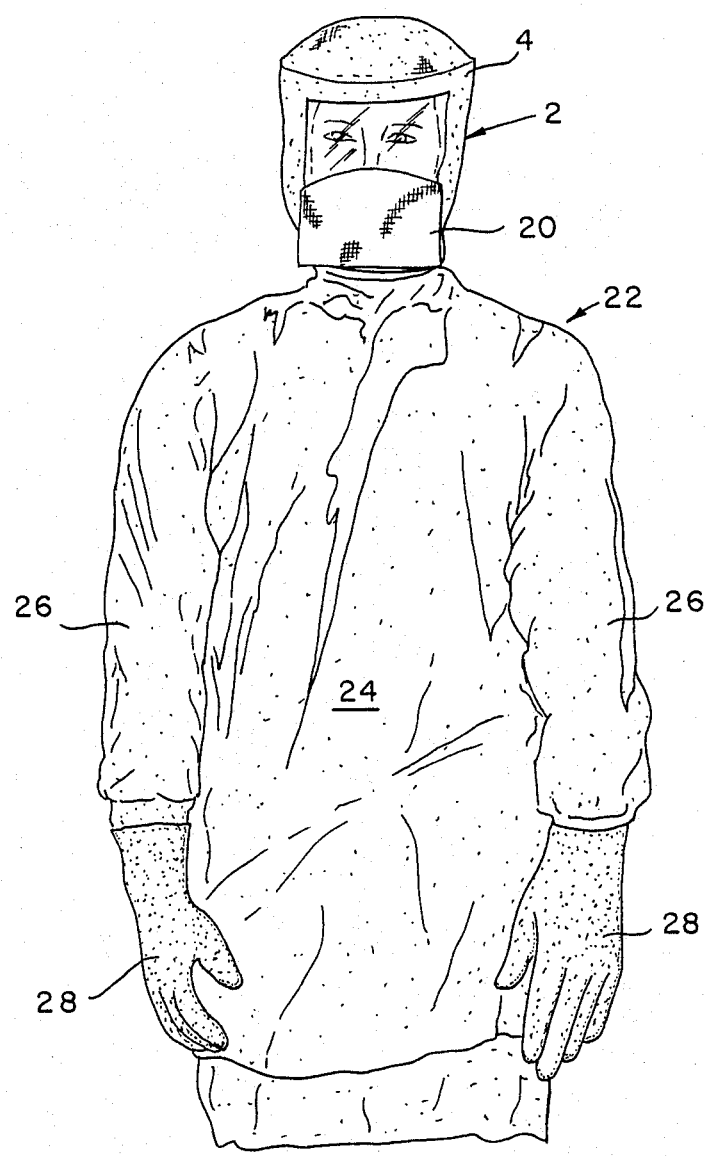
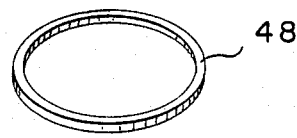
FIG. 9

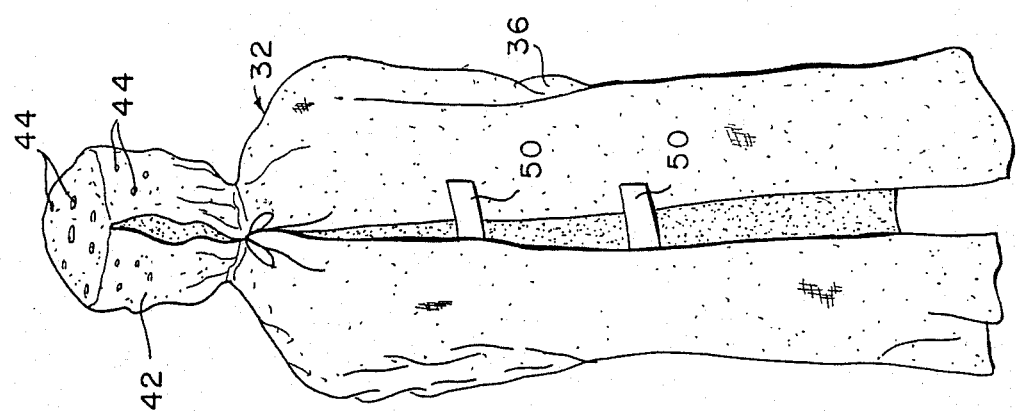
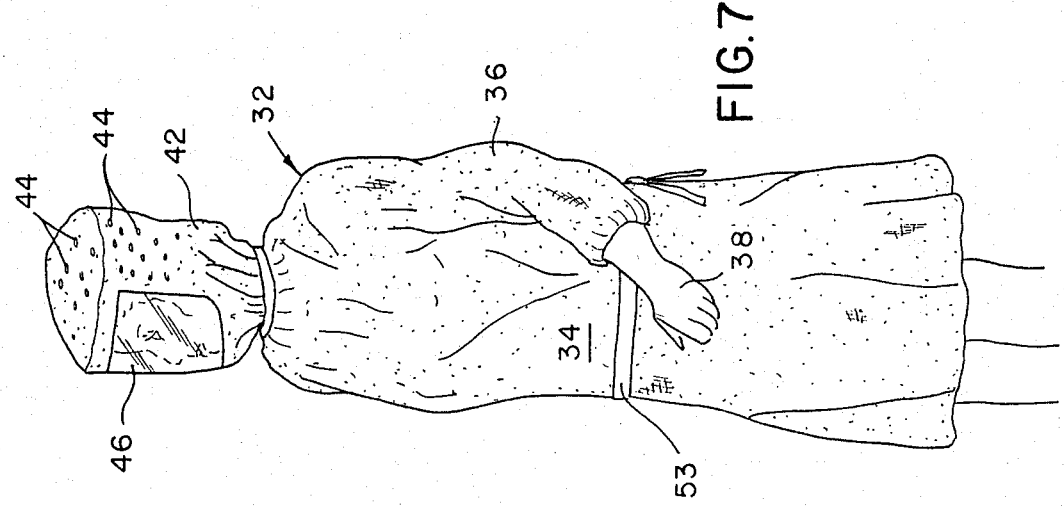
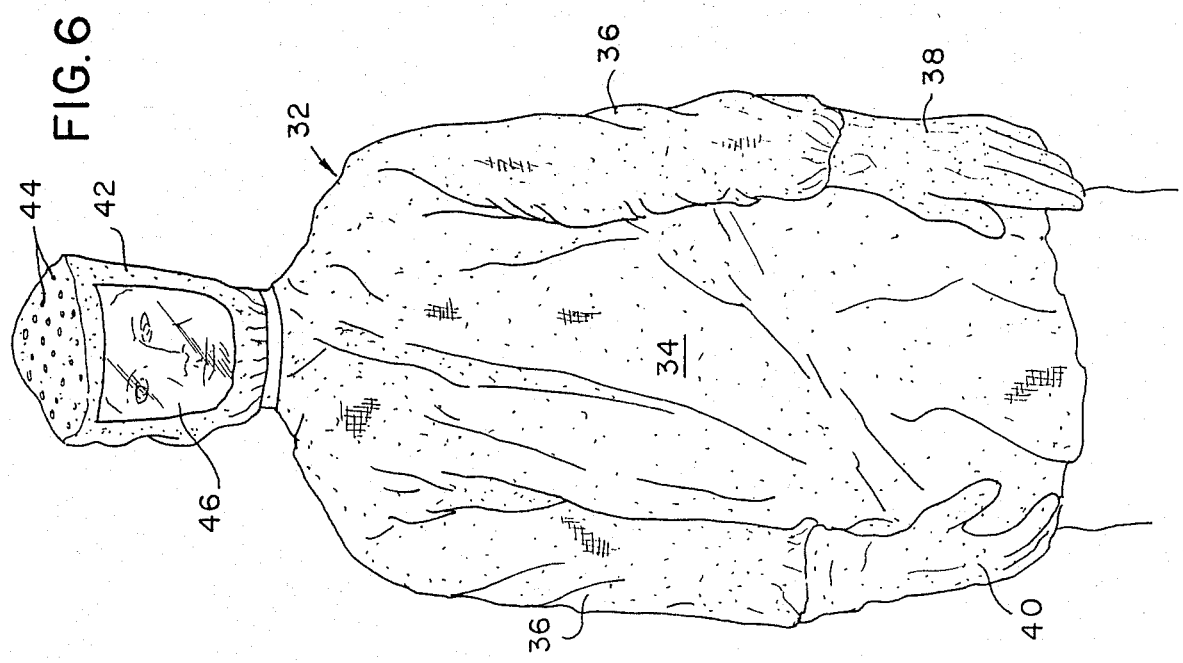

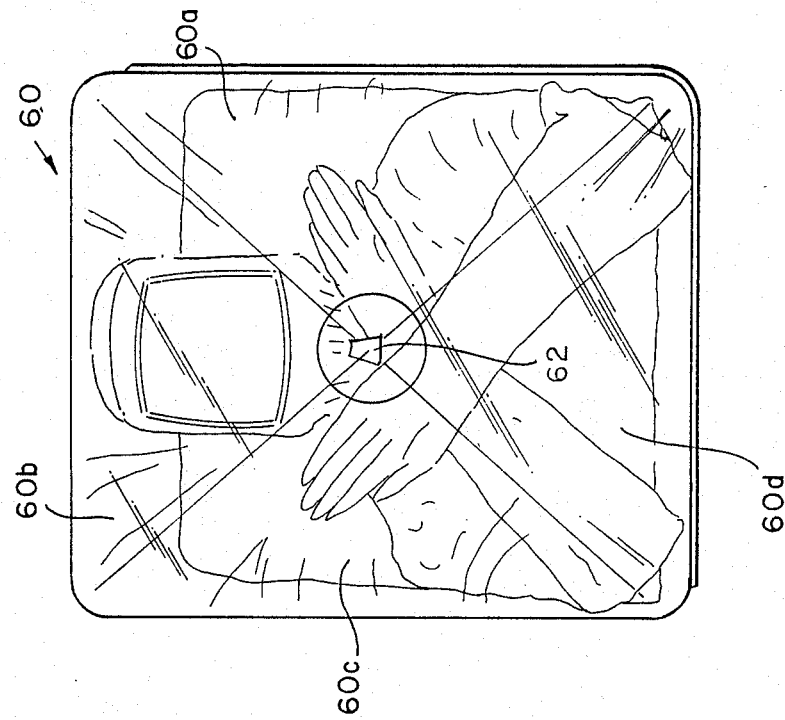
FIG.14
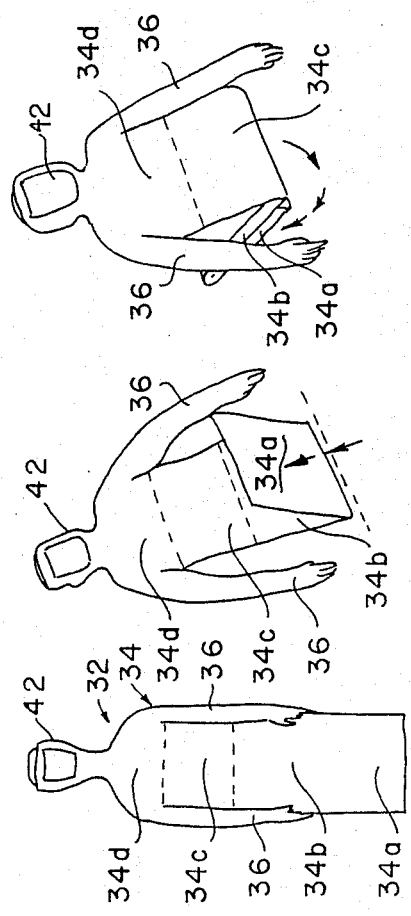
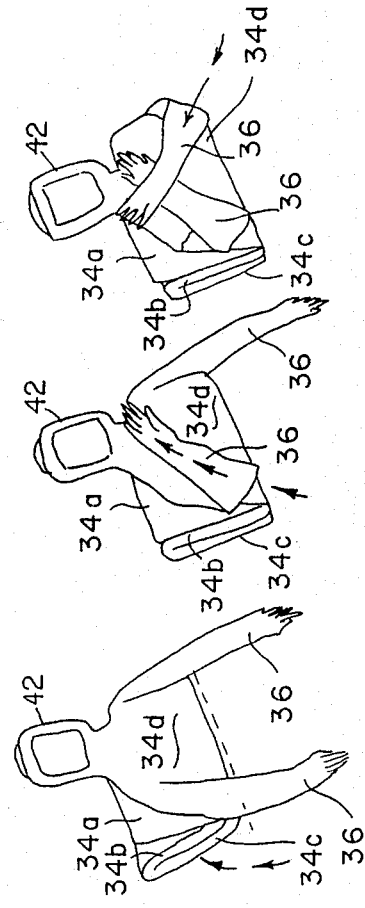
FIG.13a FIG.13b FIG.13c
FIG.13d FIG.13e FIG.13f

PROTECTIVE HOSPITAL GOWN

This application is a continuation-in-part of application Ser. No. 107,901 filed Oct. 9, 1987 which was a continuation-in-part of application Ser. No. 091,755 filed Sept. 1, 1987, both of which are now abandoned.

BACKGROUND OF THE INVENTION

Infection from AIDS and other viruses which are transmitted via bodily fluids has increased the need for protection of medical and rescue workers from contact with such fluids. The present invention relates to a disposable unitary protective garment which completely protects the wearer from contact with blood and other transmissive fluids from a patient while simultaneously protecting the patient from infection by the wearer of the gown.

BRIEF DESCRIPTION OF THE PRIOR ART

Protective hospital gowns are well known in the patented prior art. For example, combined gown and glove assemblies are disclosed in the U.S. patents to Grengg U.S. Pat. No. Des. 208,527 and Abilgaard U.S. Pat. No. 3,045,815. Protective gowns including a hood portion are disclosed in the U.S. patents to Kelly U.S. Pat. No. 1,560,997, Boettcher U.S. Pat. No. 2,374,643, Herzig U.S. Pat. No. 3,496,572, and Knab U.S. Pat. No. 4,055,173. The Kelly, Herzig, and Knab patents also disclose visors connected with the hood portions. Finally, disposable gowns are disclosed in the patents to Ramirez U.S. Pat. No. 3,855,635, Benevento et al U.S. Pat. No. 3,911,499, Toth U.S. Pat. No. 4,408,357, and White U.S. Pat. No. 4,586,196.

While the prior protective gowns are satisfactory, none of them provide a unitary construction including a hood portion sealed to the gown to completely guard the wearer against infection from a patient. Thus, blood splattered from a patient may seep through the seams between the gown and the hood or gloves and come into contact with the wearer, thereby increasing the risk of infection.

The present invention was developed in order to overcome these and other drawbacks of prior gowns by providing a unitary disposable hood and gown including sealed seams between the hood and body portions thereof to completely envelop the wearer and guarantee that no seepage of fluids from a patient may occur through the gown.

SUMMARY OF THE INVENTION

Accordingly, it is a primary object of the present invention to provide a unitary disposable gown for protecting medical personnel from infection and germs transmitted by bodily fluids. The gown comprises at least a head covering portion including a hood formed of a barrier cloth material and having a generally conical configuration open at its bottom end to allow the hood to be placed over the wearer's head. The hood contains an enlarged viewing opening in the front portion for receiving a clean synthetic plastic visor which is connected with the hood in sealed relation. A mask is also arranged in the enlarged viewing opening of the hood below the visor and is connected with both the hood and visor. The mask is formed of gauze material and may contain an opening in the top central portion thereof aligned with the wearer's nose. A protective flap formed of barrier cloth material is connected with the outer surface of the visor adjacent the mask. The flap hangs over the mask, whereby the wearer's head is covered completely by protective barrier material.

According to a further object of the invention, a protective gown formed of the barrier cloth material is connected with the lower front edge of the head covering hood. The gown includes a body portion for covering at least the torso of the wearer and a pair of arm portions connected at one end with the body portion.

According to another object of the invention, a cloth like belt is connected with both the hood and the gown body portions for tightening the hood and the body portion about the neck and torso, respectively, of the wearer to hold the gown on the wearer.

It is yet another object of the invention to provide a pair of leg and foot portions extending from the body portion of the gown.

According to another object of the invention, a pair of surgical gloves is connected in sealed relation with the other ends of the arm portions, respectively.

BRIEF DESCRIPTION OF THE FIGURES

Other objects and advantages of the invention will become apparent from a study of the following specification when viewed in the light of the accompanying drawing, in which:

FIG. 5 is a front plan view of the hood of FIGS. 2-4 connected with a protective gown as worn by an individual;

FIGS. 6, 7, and 8 are front, side, and rear plan views of an alternate embodiment of the inventive gown as worn by medical or rescue personnel;

FIG. 9 is a front perspective view of the plastic stay which is connected with the head portion of the gown;

FIGS. 13a—13f are plan views illustrating the folding sequence for packaging the gown; and FIG. 14 is a plan view of the folded packaged gown.

DETAILED DESCRIPTION

Referring first to FIGS. 1-4, there is shown the disposable protective head covering 2 according to the invention. The head covering includes a hood 4 formed of a barrier cloth material such as a blend of polyester and pulp material. The term barrier is used to describe a material which is impervious to germs or infections transmitted by bodily fluids.

Figure 1:
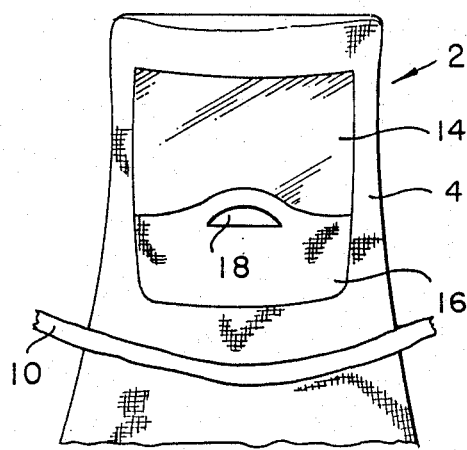
FIGS. 1 and 2 are front plan views of the protective disposable hood according to a preferred embodiment of the invention with the protective flap removed and attached, respectively.
Figure 2:
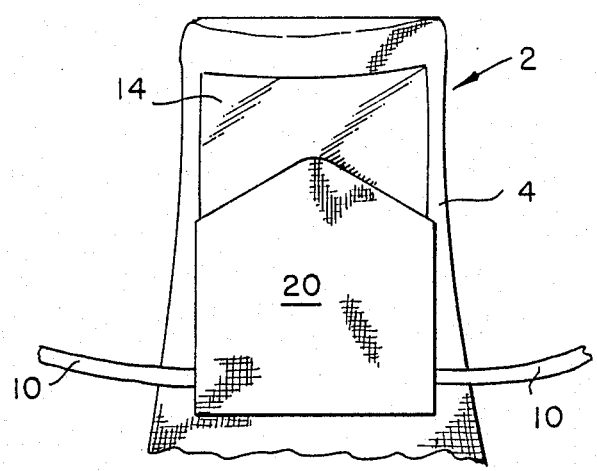
Figure 3:
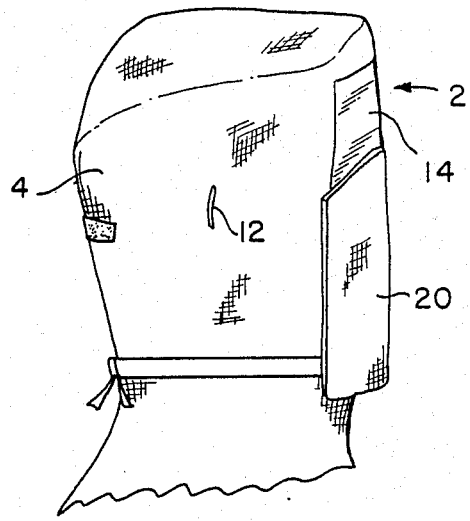
FIGS. 3 and 4 are side and rear views, respectively, of the hood of FIG. 2.
Figure 4:
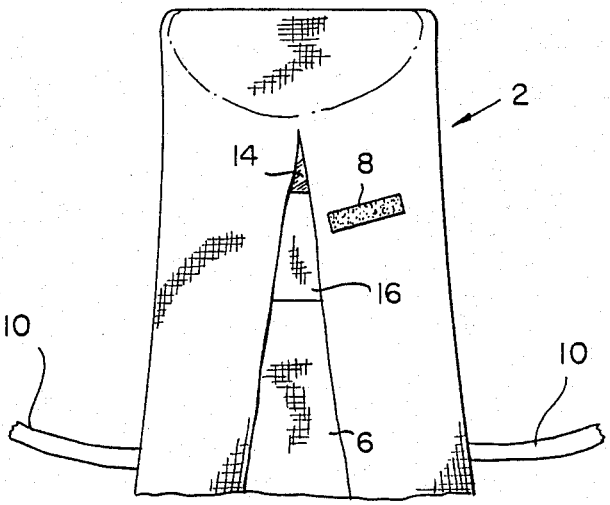

As shown in FIGS. 1, 2, and 4, the hood has a generally conical configuration and is open at its bottom end. The rear portion of the hood contains a vertical slit 6. The opening at the hood bottom and the vertical slit 6 enable the hood to be placed over the head of the wearer. A piece of tape 8 or other fastening device such as a VELCRO fastener is connected with the hood adjacent to the slit to close the slit when the hood is on the wearer's head. Furthermore, a pair of cloth ties 10 are connected with the hood and tied around the wearer's neck as shown in FIG. 3 to hold the hood in place and to enclose the wearer's head and neck. Small perforations 12 are provided in the sides of the hood to receive the ends of a stethoscope or the like for placement in the wearer's ears.

Referring once again to FIG. 1, the front portion of the hood contains an enlarged viewing opening for receiving in the top portion thereof a clear visor 14 formed of synthetic plastic material, clear acetate or any other inexpensive impervious material. The visor is heat sealed about its peripheral edge to the hood adjacent to the opening and is arched about the bridge of the nose of the wearer. The lower portion of the opening is covered by a mask 16 preferably formed of gauze material (0.6 oz. fabric) and heat sealed by a conventional hot melt adhesive to the edge of the hood adjacent to the opening and to the lower edge of the visor. The mask preferably contains an opening 18 in the top central portion thereof which is arranged adjacent the wearer's nose when the covering is in place on the wearer's head. In this manner, adequate ventilation is provided to the interior of the head covering preventing overheating of the wearer and fogging of the visor. In lieu of the gauze mask, a conventional surgical mask may be used.

Referring now to FIG. 2, there is shown a protective flap 20 formed of barrier cloth material and connected with the visor in sealed relation adjacent the mask, whereby the flap extends downwardly completely covering the mask. With the flap in place, a complete barrier is provided to the wearer's head and neck preventing infection from contacting the wearer's eyes, nose, mouth, ears, and the like. To maintain the flap in place, the lower corners of the flap may be adhesively connected with the hood by a spot tack or weld of hot melt material. As shown in FIGS. 1 and 2, the mask 16 and flap 20 both taper downwardly from the central portion of the visor to the sides thereof to increase the field of vision of the wearer.

Figure 10:
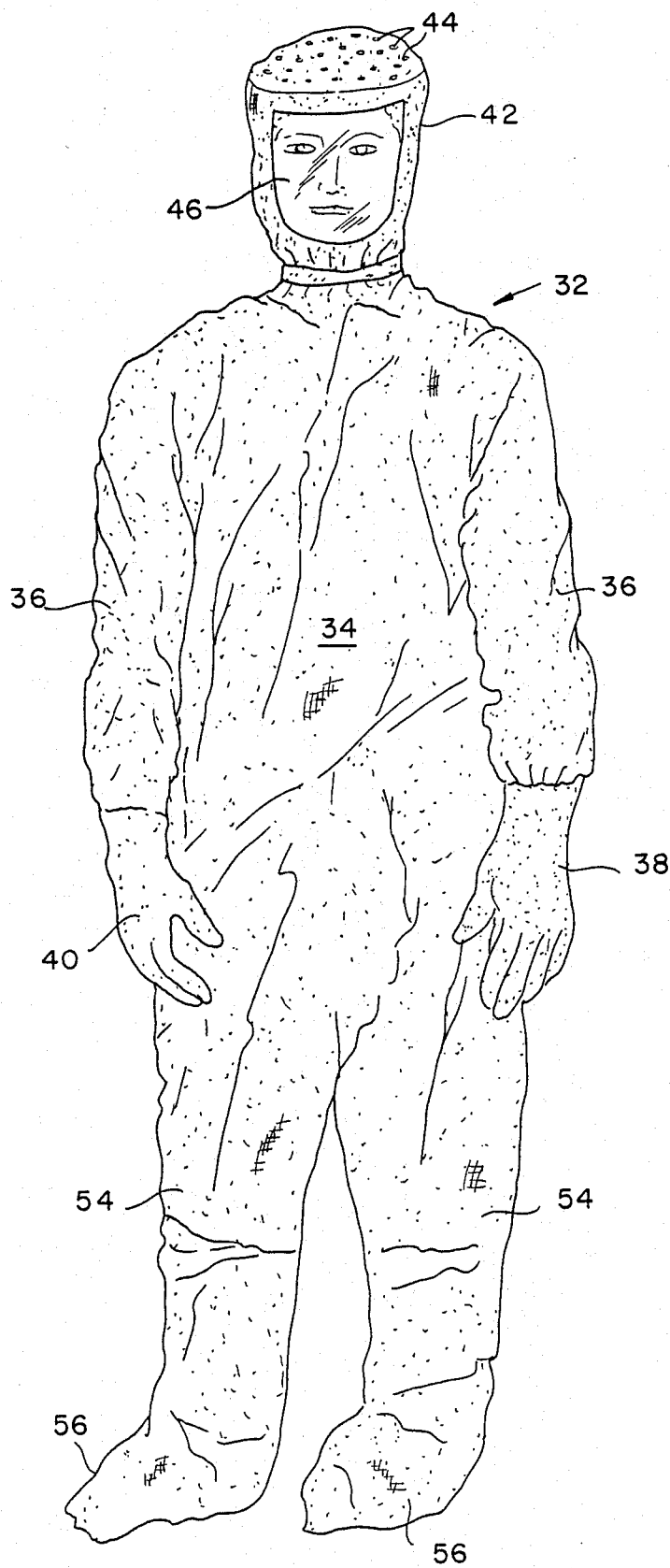
FIG. 10 is a front plan view of a further embodiment of the gown of FIGS. 6-8 including leg and foot portions.

It will be appreciated that the head covering 2 of FIGS. 1-4 may have any desired length to cover additional portions of the wearer's body. For ease of fit and maximum comfort and protection, the lower front edge of the head covering may be connected with a protective gown 22 and worn as shown in FIG. 5. The protective gown is also formed of a disposable barrier cloth material and includes a generally cylindrical body portion 24 and a pair of arm portions 26 connected at one end with the body portion. The gown may also include leg and foot portions as shown in FIG. 10 and as will be discussed more fully below.

A pair of surgical gloves 28 is sealingly connected with the other ends of the arm portions. The head covering 2, gown 22, and gloves 28 thus comprise a unitary disposable garment affording complete protection from infectious diseases. In lieu of the surgical gloves, the remote ends of the arm portions may be provided with elastic or extended cloth cuffs, with separate gloves being worn thereover.

Referring now to FIGS. 6-8, an alternate embodiment of the disposable protective medical gown of the invention will be described. The gown 32 includes a main body portion 34 having a generally cylindrical configuration for covering at least the torso of the wearer. Of course, the length of the body portion may be increased to cover the wearer's legs if desired.

Connected with the body portion 34 are a pair of arm portions 36 which may either be integrally formed with the body portion or sealingly connected therewith to maintain a unitary structure. At the remote end of each arm is connected a glove, with a left-handed glove 38 being connected with the left arm portion and a right-handed glove 40 connected with the right arm portion. The gloves are preferably surgical rubber gloves to provide the appropriate degree of dexterity to the wearer. The gloves are also connected with the respective arm portions in sealed relation, either by stitching or preferably through a heat seal, whereby the gloves are not detachable from the gown arm portions. Alternatively, separate surgical gloves may be provided. A hood portion 42 is connected with the own body portion at the top of the gown between the arm portions. The hood may also be formed integrally with the gown to ensure that there is an impervious seal between the hood and body portions as there is between the body and arm portions and between the arm portions and gloves. The neck area of the gown between the hood and body portions may be gathered with a strip of elastic material so that it fits snugly around the neck of the wearer.

The hood portion 42 contains a plurality of ventilating openings 44 in at least the top surface of the hood and also in the rear portion thereof, if desired. The openings enable the wearer to breath normally and also serve to allow heat generated by the wearer to escape the hood. An enlarged viewing opening is contained in the front surface of the hood portion and receives a clear synthetic plastic visor 46 which is secured about its edges with the hood about the periphery of the enlarged opening in sealing relation, whereby this seam is also impervious to fluids.

At the juncture between the top and side surfaces of the hood portion 42 there is provided a pocket (not shown) for receiving a circular synthetic plastic stay 48 shown in FIG. 9. The stay, which has a diameter slightly greater than the diameter of the wearer's head, serves to space the side front and rear surfaces of the hood portion from the wearer's head, to increase the comfort of the gown.

The bottom of the gown body portion 34 is open to allow the gown to be pulled over the wearer's head and down the wearer's body to completely cover the upper portion of the wearer. Preferably, the rear of the gown body portion contains a vertical opening, enabling the gown to be more easily put on and taken off by the wearer.

At the rear of the gown are provided a plurality of fastening devices 50 for closing the vertical opening in the body portion as shown in FIG. 8. The fastening devices, which may comprise adhesive strips or VELCRO type fasteners, help to keep the gown on the wearer to improve the fit, and also to keep loose portions of the gown from inhibiting the wearer or contacting the patient. A drawstring 52 is also provided to adjust and tighten the elastic neck portion of the gown.

A pair of ties 53 are connected with the front of the gown body portion and tied together in the rear to further help keep the gown on the wearer.

The body, arm, and hood portions of the gown are preferably formed as an integral structure from a single piece of lightweight durable barrier fabric such as paper or synthetic plastic or rubber which has been treated with gamma radiation for sterilization.

In the embodiment shown in FIG. 10, the gown 32 is in effect configured as a protective suit or garment including leg portions 54 terminating in foot portions 56 which are formed integrally with the gown body portion 34. The leg and foot portions further protect the wearer from spillage of blood or from contaminants on the floor.

Figure 11:
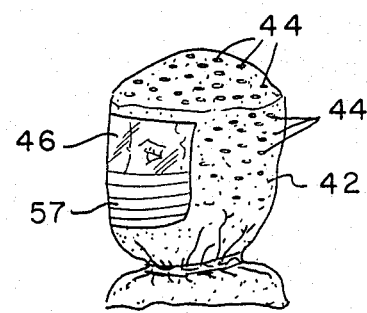
FIGS. 11 and 12 are partial side and front views, respectively, of the gown hood portion including a surgical mask provided within the opening thereof beneath the visor.
Figure 12:
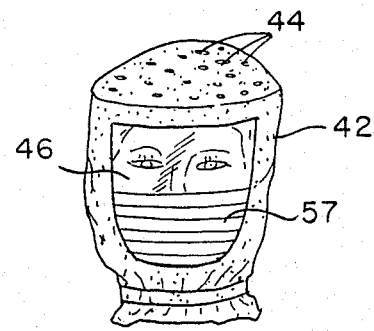

Referring now to FIGS. 11 and 12, an alternate configuration of the visor 46 is shown. More particularly, the visor fills the top area of the enlarged opening provided in the hood portion 42. A surgical mask 57 fills the bottom area of the enlarged opening and is preferably arranged opposite the nose and mouth of the wearer to facilitate ventilation within the gown hood portion. The upper edge of the mask is preferably heat sealed to the lower edge of the visor so that the juncture therebetween is impervious to fluid. The remaining edges of the mask 57 are stitched or sealed to the hood portion at edges of the enlarged opening, whereby the mask is part of the unitary gown assembly.

Packaging of the sterilized gown is shown more particularly in FIGS. 13-14. Referring first to FIG. 13a, the gown 32 is shown in its unfolded condition, with the body portion 34 being divided into four sections, i.e. lower section 34a, lower intermediate section 34b, upper intermediate section 34c, and upper section 34d. To compactly fold the gown for packaging, the lower section 34a is folded forwardly and upwardly against the lower intermediate section 34b as shown in FIG. 13b. Next, the folded sections 34a and 34b are reversely folded once against upper intermediate section 34c (FIG. 13c) and a second time against upper section 34d (FIG. 13d). Next, the arm portions 36 are sequentially folded across the front of the body upper portion 34d as shown in FIGS. 13e and 13f. The sterile gown is then sealed within an impervious synthetic plastic package 60 as shown in FIG. 14. The package includes folded portions 60a–60d which are opened by a pull tab 62. The hood portion 42 of the gown is then drawn from the package with the remainder of the gown following.

From the above, it is apparent that the disposable gown and hood will provide maximum protection to the wearer from contact with body fluids from a patient since both are of a unitary construction and all seams thereof are impervious to fluid. The gown and hood are durable, lightweight, and inexpensive, providing safety and comfort to the wearer, following which they are disposed of after a single use. In this manner, any germs which come into contact with the gown and hood are safely disposed of, without physical contact with the wearer.

The protective gown and hood which may be made in different standard sizes such as small, medium, large, and extra large, are suitable for use by individuals of any profession that might come into direct contact with bodily fluids from the public. These include doctors, nurses, laboratory technicians, paramedics, policemen, firemen, coroners, morticians, home health care aides, veterinarians, dentists, health officials, and the like.

It is understood by those of ordinary skill in the art that the features of one embodiment disclosed herein may be used interchangeably on other embodiments to achieve similar results.

While in accordance with the provisions of the patent statute the preferred forms and embodiments of the invention have been illustrated and described, it will be apparent to those skilled in the art that various changes and modifications may be made without deviating from the inventive concepts set forth above.

What is claimed is:

1. A disposable head covering for protecting medical personnel from infection and germs transmitted by bodily fluids, comprising
    (a) a hood formed of a barrier cloth material and having a generally conical configuration open at its bottom end, whereby said hood may be placed over the wearer's head, said hood containing an enlarged viewing opening in the front portion thereof;
    (b) a visor arranged within the top portion of said enlarged viewing opening and connected in sealed relation with said hood;
    (c) a mask arranged within the bottom portion of said enlarged viewing opening and connected in sealed relation with the lower edge of said visor and with said hood; and
    (d) a protective flap formed of barrier cloth material connected in sealed relation with said visor adjacent to the connection between said visor and said mask, said flap covering at least said mask, whereby the wearer's head is covered completely by protective barrier material.

2. A head covering as defined in claim 1, wherein said mask contains an opening in the top central portion thereof, whereby when said hood is placed over the wearer's head, the wearer's nose is aligned with said mask opening.

3. A head covering as defined in claim 2, and further comprising tie means connected with said hood for tightening said hood around the neck of the wearer to hold the covering on the wearer's head.

4. A head covering as defined in claim 3, wherein said hood contains a vertical slit in the rear portion thereof, and further comprising means connected with said hood for closing said slit.

5. A head covering as defined in claim 4, wherein said visor is formed of clear synthetic plastic material.

6. A head covering as defined in claim 5, wherein said barrier cloth material comprises a blend of polyester and pulp materials.

7. A head covering as defined in claim 6, wherein said mask is formed of gauze material.

8. A head covering as defined in claim 7, wherein a hot melt adhesive is used for said sealed connections.

9. A head covering as defined in claim 6, wherein said hood contains a pair of slits in the side portions thereof, respectively, adjacent to the ears of the wearer to receive the ends of a stethoscope.

10. A unitary, disposable medical gown, comprising
    (a) a generally cylindrical body portion adapted for covering at least the torso of the wearer;
    (b) a pair of arm portions connected at one end with said body portion;
    (c) a hood connected with the front upper edge of said body portion between said arm portions, said hood having a generally conical configuration open at its bottom end, whereby said hood may be placed over the wearer's head, said hood containing an enlarged viewing opening in the front portion thereof;
    (d) a visor arranged within the top portion of said enlarged viewing opening and connected in sealed relation with said hood;
    (e) a mask arranged within the bottom portion of said enlarged viewing opening and connected in sealed relation with the lower edge of said visor and with said hood; and (f) a protective flap formed of barrier cloth material connected in sealed relation with said visor adjacent to the connection between said visor and said mask, said flap covering at least said mask, whereby the wearer's head is covered completely by protective barrier material.

11. A medical gown as defined in claim 10, wherein said mask contains an opening in the top central portion thereof, whereby when said hood is placed over the wearer's head, the wearer's nose is aligned with said mask opening.

12. A medical gown as defined in claim 11, wherein said body portion, said arm portions, said hood, and said flap are formed of a barrier cloth material.

13. A medical gown as defined in claim 12, and further comprising tie means connected with said hood and with said body portion for tightening said hood and said body portion about the neck and torso, respectively, of the wearer to hold the gown on the wearer.

14. A medical gown as defined in claim 13, wherein said hood contains a vertical slit in the rear portion thereof, and further comprising means connected with said hood for closing said slit.

15. A medical gown as defined in claim 14, wherein said visor is formed of clear synthetic plastic material.

16. A medical gown as defined in claim 15, wherein said mask is formed of gauze material.

17. A medical gown as defined in claim 16, wherein said hood contains a pair of slits in the side portions thereof, respectively, adjacent to the ears of the wearer to receive the ends of a stethoscope.

18. A medical gown as defined in claim 12, and further comprising a pair of gloves connected in sealed relation with the other ends of said arm portions, respectively.

19. A medical gown as defined in claim 12, and further comprising a pair of leg and foot portions extending from the bottom of said body portion.

20. A unitary, disposable, hospital gown, comprising
 (a) a generally cylindrical body portion adapted for covering at least the torso of the wearer;
 (b) a pair of arm portions connected at one end with said body portion;
 (c) a hood portion connected in sealed relation with the upper edge of said body portion between said arm portions, said hood portion containing a plurality of ventilation openings in the top portion thereof and an enlarged viewing opening in the front portion thereof; and
 (d) visor means arranged within said enlarged viewing opening and connected in sealed relation with said hood portion, whereby the gown provides protection to the wearer from infection and germs transmitted by bodily fluids.

21. A hospital gown as defined in claim 20, wherein said body portion has a vertical opening at the rear thereof, and further comprising fastening means connected with said body portion for closing said rear vertical opening.

22. A hospital gown as defined in claim 21, and further comprising a generally circular stay connected with said hood portion adjacent the upper surface thereof to space said hood portion and said visor means from the wearer's face.

23. A hospital gown as defined in claim 21, and further comprising a pair of surgical gloves connected with the other ends of said arm portions, respectively.

24. A hospital gown as defined in claim 23, wherein said gloves are sewn to the other ends of said arm portions, respectively.

25. A hospital gown as defined in claim 23, wherein said gloves are heat sealed to the other ends of said arm portions, respectively.

26. A hospital gown as defined in claim 23, wherein said visor means is formed of transparent synthetic plastic material.

27. A hospital gown as defined in claim 26, wherein said visor means is heat sealed to said hood portion.

28. A hospital gown as defined in claim 27, and further comprising a pair of leg and foot portions extending from the bottom of said body portion.

29. A hospital gown as defined in claim 28, and further comprising mask means arranged within said enlarged viewing opening below said visor means and connected in sealed relation with said visor means and said hood portion.

30. A hospital gown as defined in claim 29, wherein said body, arm, hood, leg and foot portions are formed of a barrier cloth material.

31. A hospital gown as defined in claim 29, wherein the area between said hood and body portions is elastically gathered about the neck of the wearer.

32. A hospital gown as defined in claim 31, wherein the area between said hood and body portion contains a drawstring for adjusting the elastic portion about the neck of the wearer.

33. A hospital gown as defined in claim 29, wherein said body, arm, hood, leg and foot portions are treated with gamma radiation for sterilization.

34. A hospital gown as defined in claim 33, wherein said sterilized gown is folded and wrapped individually in a sterile package.

* * * * *